United States Patent [19]

Nakanura

[11] Patent Number: 5,292,420
[45] Date of Patent: Mar. 8, 1994

[54] TWO-DIMENSIONAL GEL ELECTROPHORESIS APPARATUS

[75] Inventor: Shin Nakanura, Kyoto, Japan

[73] Assignee: Shimadzu Corporation, Kyoto, Japan

[21] Appl. No.: 853,395

[22] Filed: Mar. 17, 1992

[30] Foreign Application Priority Data

Mar. 29, 1991 [JP] Japan .................................. 3-93710

[51] Int. Cl.$^5$ ..................... G01N 27/26; G01N 27/447
[52] U.S. Cl. .............................. 204/299 R; 204/182.1; 204/182.8
[58] Field of Search .............. 204/182.1, 182.8, 299 R

[56] References Cited

U.S. PATENT DOCUMENTS 4,305,799 12/1981 Schwarz et al. ............ 204/299 R X
4,966,667 10/1990 Rising et al. ...................... 204/182.1

FOREIGN PATENT DOCUMENTS 58-53745 3/1983 Japan .

OTHER PUBLICATIONS

Denis Hochstrasser et al "High–Resolution Mini-Two–Dimensional Gel Electrophoresis Automatically Run and Stained in <6 h with Small, Ready-to-Use Slab Gels" Clin. Chem. 34/1 (1988) 166–170.

Primary Examiner—John Niebling
Assistant Examiner—John S. Starsiak, Jr.
Attorney, Agent, or Firm—William L. Klima

[57] ABSTRACT

Disclosed herein is a two-dimensional electrophoresis apparatus comprising a first-dimensional electrophoresis part (5), a second-dimensional electrophoresis part (6) and a transcription part (7). The transcription part (7) transfers a first-dimensional gel completely electrophoresed by the first-dimensional electrophoresis part (5) from a first-dimensional gel housing (20) to one end of a second-dimensional gel housing (30). Thus, a two-dimensional electrophoresis can be automatically executed, thereby improving reproducibility of separated images and separative power.

13 Claims, 10 Drawing Sheets

TWO-DIMENSIONAL GEL ELECTROPHORESIS APPARATUS

BACKGROUND OF THE INVENTION

1. Field of the Invention

The present invention relates to an electrophoresis apparatus, and more particularly, it relates to a two-dimensional electrophoresis apparatus for making a two-dimensional electrophoresis with a first-dimensional gel housing which stores a first-dimensional gel and a second-dimensional gel housing which stores a second-dimensional gel.

2. Description of the Background Art

In general, a two-dimensional electrophoresis method is carried out in the following procedure: First, a first-dimensional gel is formed in a glass tube, to make a first-dimensional electrophoresis in relation to a sample such as protein with the first-dimensional gel. Then, the first-dimensional gel, in which the sample is separated and fractionated through the first-dimensional electrophoresis, is connected to a second-dimensional slab gel which is previously formed between two glass plates, to make a second-dimensional electrophoresis while transferring the sample fractions to the second-dimensional gel.

In a conventional two-dimensional electrophoresis method, such electrophoresis steps are manually carried out by an operator. Thus, it takes great skill to handle the gels, while the respective operations are complicated. Therefore, it is difficult to improve reproducibility of separated images and separative power.

SUMMARY OF THE INVENTION

An object of the present invention is to provide a two-dimensional electrophoresis apparatus which can improve reproducibility of separated images and separative power by enabling automatic implementation of a two-dimensional electrophoresis.

The two-dimensional electrophoresis apparatus according to the present invention is adapted to make a two-dimensional electrophoresis with a first-dimensional gel housing which stores a first-dimensional gel and a second-dimensional gel housing which stores a second-dimensional gel. This apparatus comprises first-dimensional electrophoresis means, second-dimensional electrophoresis means, and gel transfer means.

The first-dimensional electrophoresis means is adapted to make a first-dimensional electrophoreis of the first-dimensional gel. The second-dimensional electrophoreis means is adapted to make a second-dimensional electrophoresis of the second-dimensional gel. The gel transfer means is adapted to transfer the first-dimensional gel, completing the electrophoreis by the first-dimensional electrophoresis means, from the first-dimensional gel housing to one end of the second-dimensional gel housing.

In the two-dimensional electrophoresis apparatus according to the present invention, the first-dimensional electrophoresis means makes a first-dimensional electrophoreis of the first-dimensional gel. Then, the gel transfer means transfers the first-dimensional gel, completing the electrophoresis by the first-dimensional electrophoresis means, from the first-dimensional gel housing to an end of the second-dimensional gel housing. Thus, the first-dimensional gel, containing a sample such as protein being separated and fractionated by the first-dimensional electrophoresis, is connected to the second-dimensional gel. Then the second-dimensional electrophoresis means makes a second-dimensional electrophoresis of the second-dimensional gel. Thus, the sample fractions are transcribed from the first-dimensional gel to the second-dimensional gel, which in turn are subjected to a second-dimensional electrophoreis. Since the gel transfer means transfers the first-dimensional gel from the first-dimensional gel housing to the end of the second-dimensional gel housing, reproducibility of separated images and separative power are improved with no regard to the skill of an operator.

The foregoing and other objects, features, aspects and advantages of the present invention will become more apparent from the following detailed description of the present invention when taken in conjunction with the accompanying drawings.

DESCRIPTION OF THE PREFERRED EMBODIMENT

Figure 1:
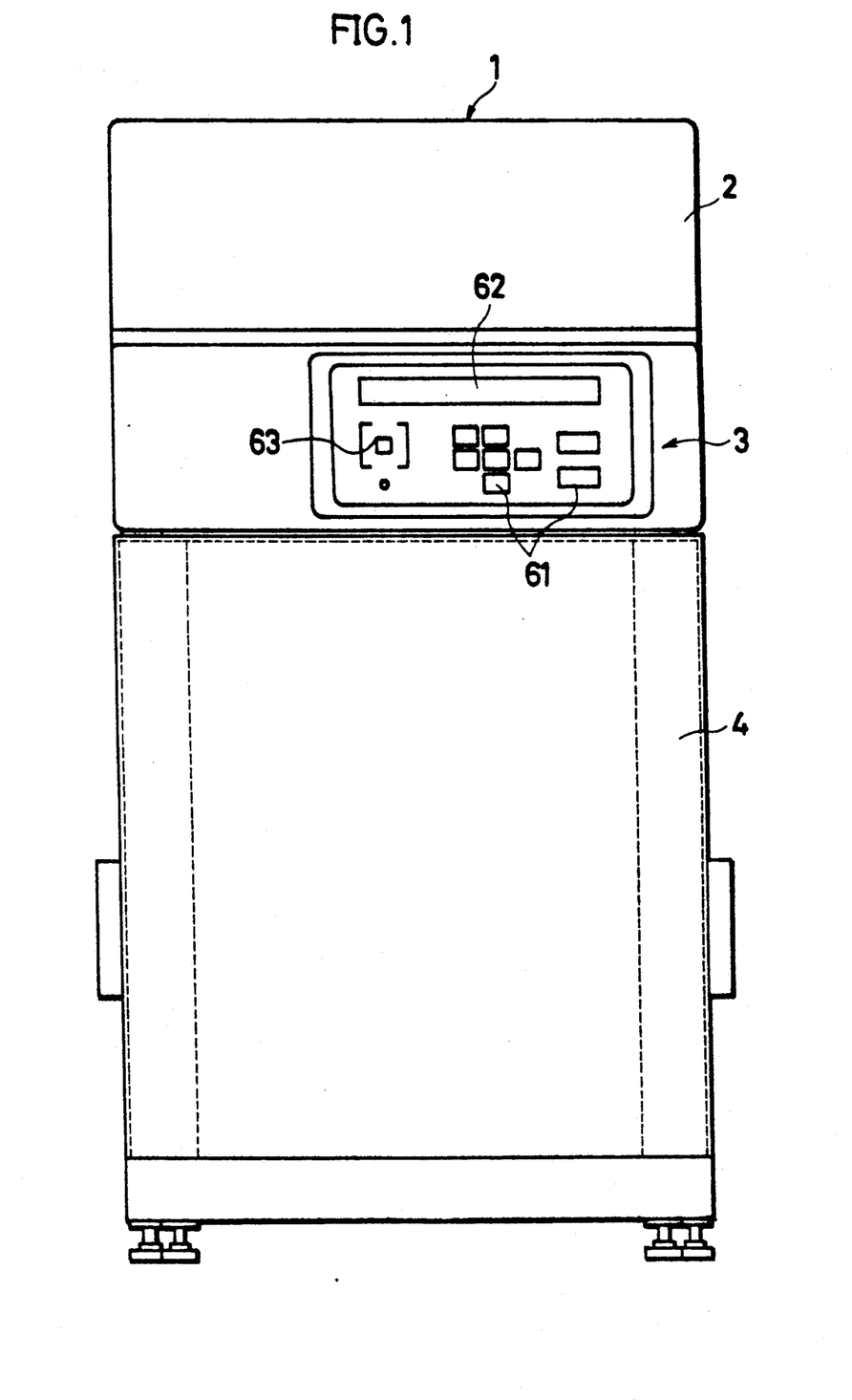
FIG. 1 is a front elevational view showing a two-dimensional electrophoresis apparatus according to an embodiment of the present invention.

FIG. 1 shows a two-dimensional electrophoresis apparatus 1 according to an embodiment of the present invention. This two-dimensional electrophoresis apparatus 1 has an apparatus body 2, a control panel 3 which is arranged on the front surface of the apparatus body 2, and a front door 4 which is arranged under the control panel 3. The front door 4 is openable, so that an operator can approach a mechanism which is arranged in the apparatus body 2.

Figure 2:
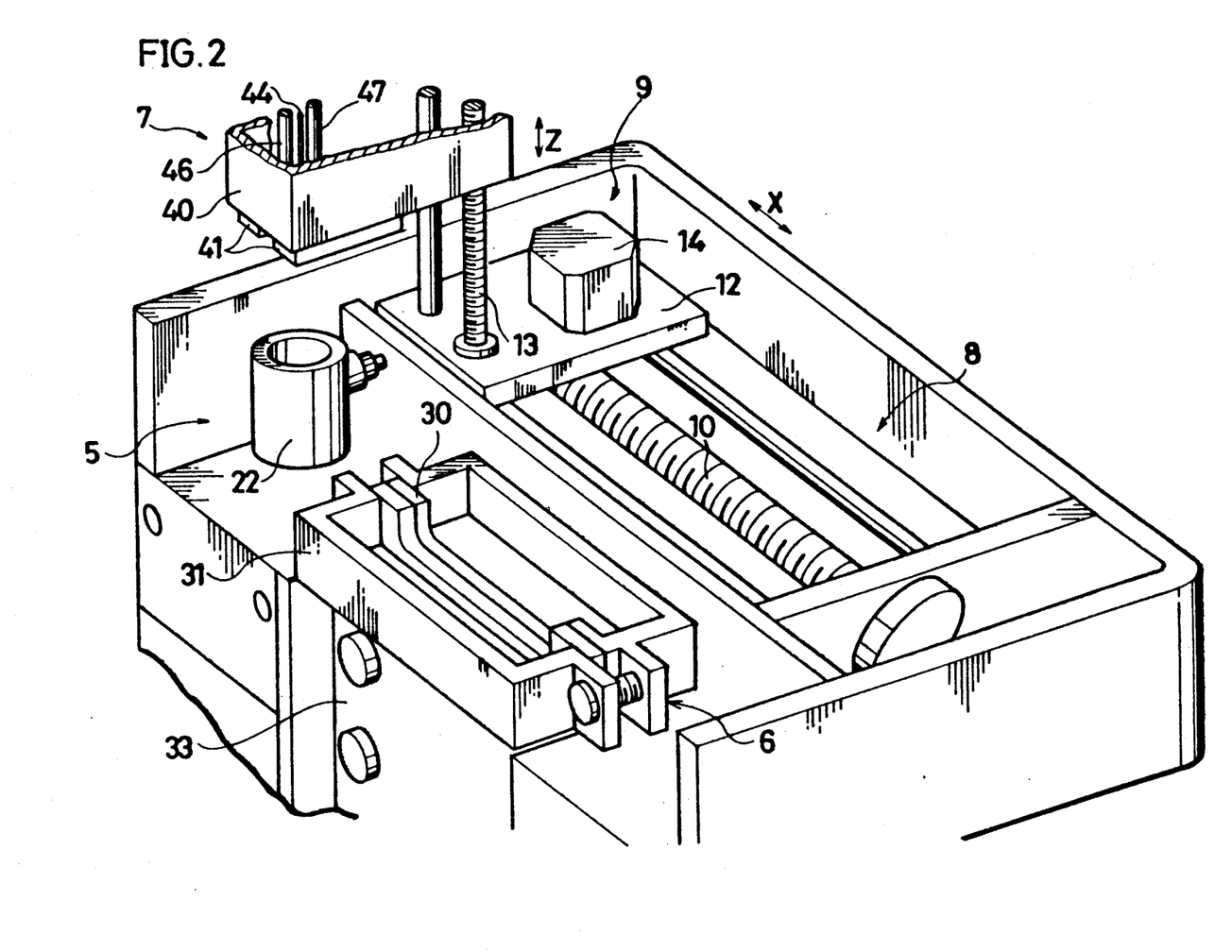
FIG. 2 is a perspective view schematically showing the internal mechanism of the electrophoresis apparatus.

FIG. 2 shows the mechanism which is arranged in the apparatus body 2. Referring to FIG. 2, a first-dimensional electrophoresis part 5 and a second-dimensional electrophoresis part 6 are arranged on this side of the apparatus 1. A transcription part 7 is arranged above these electrophoresis parts 5 and 6. Further, an X-axis driving part 8 for driving the transcription part 7 in an X-axis direction (horizontal direction) and a Z-axis driving part 9 for driving the transcription part 7 in a Z-axis direction (vertical direction) are arranged on the other side of the apparatus 1. The transcription part 7, the X-axis driving part 8 and the Z-axis driving part 9 form gel transfer means.

The X-axis driving part 8 comprises a feed screw 10 extending in the X-axis direction and a stepping motor 11 for rotating and driving the feed screw 10. The feed screw 10 is fitted with a female screw part (not shown), which is provided on a base 12 of the Z-axis driving part 9. The Z-axis driving part 9 has a feed screw 13 upwardly projecting from the base 12 and a stepping motor 14 for rotating and driving the feed screw 13. The feed screw 13 is fitted with a female screw part (not shown), which is provided on the transcription part 7.

Figure 3:
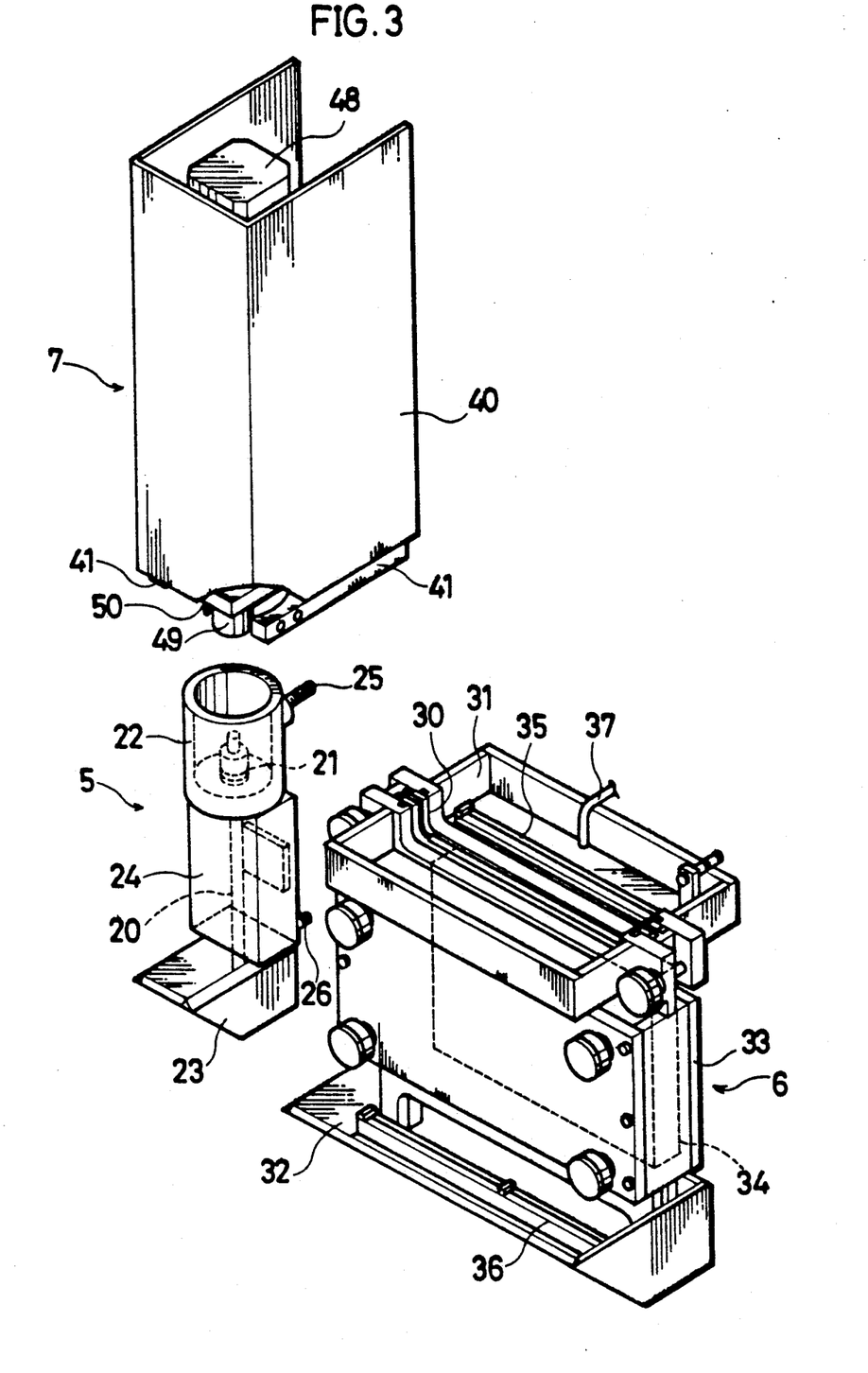
FIG. 3 is a perspective view showing a principal part of the internal mechanism.

As shown in FIG. 3, the first-dimensional electrophoresis part 5 has a housing 20 which is formed by a glass tube for storing a first-dimensional gel, a holder 21 holding the upper end of the housing 20, an upper reservoir 22 which is fixed to the holder 21, and a lower reservoir 23 receiving the lower end of the housing 20. The central portion of the housing 20 is enclosed with a temperature control block 24 which is controlled by a Peltier element. The upper and lower reservoirs 22 and 23 are provided with upper and lower electrodes 25 and 26 respectively.

The two-dimensional electrophoresis part 6 has a housing 30 which is formed by a pair of glass plates holding a planarly spread slab gel, an upper reservoir 31 which is provided on the upper portion of the housing 30, a lower reservoir 32 receiving the lower portion of the housing 30, and a clamp 33 enclosing the central portion of the housing 30. The clamp 33 is provided with a temperature control block 34, which is temperature-controlled by a Peltier element. The upper and lower reservoirs 31 and 32 are provided with upper and lower electrodes 35 and 36 respectively. The upper reservoir 31 is further provided with a supply nozzle 37 for supplying an electrode liquid to the upper reservoir 31.

Figure 4:
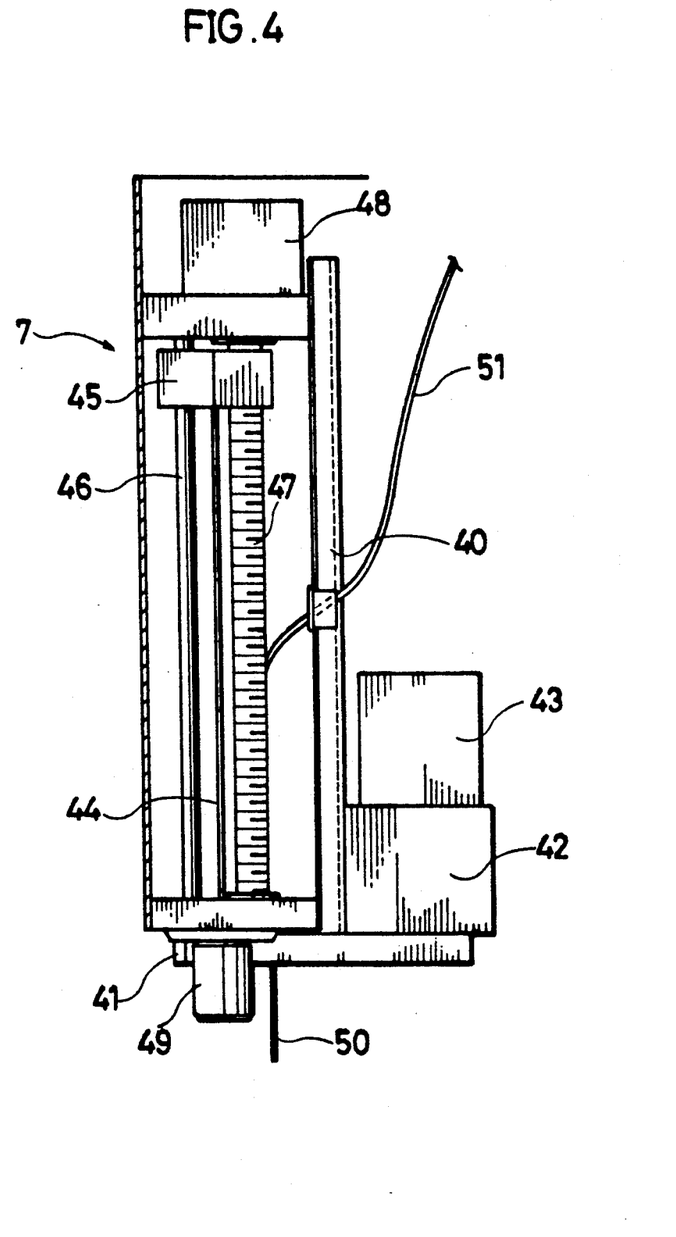
FIG. 4 is a partially fragmented longitudinal sectional view showing a transcription part of the electrophoresis apparatus.

FIG. 4 shows a structure which is provided in a frame 40 of the transcription part 7. Referring to FIG. 4, the transcription part 7 is provided on its lower portion with a chuck 41 for grasping the upper reservoir 22 (FIG. 3). This chuck 41 is opened/closed by a stepping motor 43 through a cam mechanism 42. Further, a vertically extending gel extrusion rod 44 is arranged in the frame 40. An upper end of this rod 44 is fixed to a holding plate 45, which is slidable with respect to a vertically extending guide shaft 46 and tapped for being adapted for screwing to a vertically extending feed screw 47. The feed screw 47 is rotated and driven by a stepping motor 48 which is arranged on the upper portion of the frame 40, thereby vertically moving the holding plate 45. The lower portion of the rod 44 is inserted in a centering cylindrical member 49 which is provided on the lower end portion of the frame 40. The centering cylindrical member 49 is adapted to engage with the upper end portion of the housing 20 in operation of this apparatus 1, to align center lines of the housing 20 and the gel extrusion rod 44 with each other.

The frame 40 is further provided with a downwardly projecting discharge nozzle 50 on its lower portion. This discharge nozzle 50 is coupled to a suction mechanism (not shown) through a tube 51.

Figure 5:
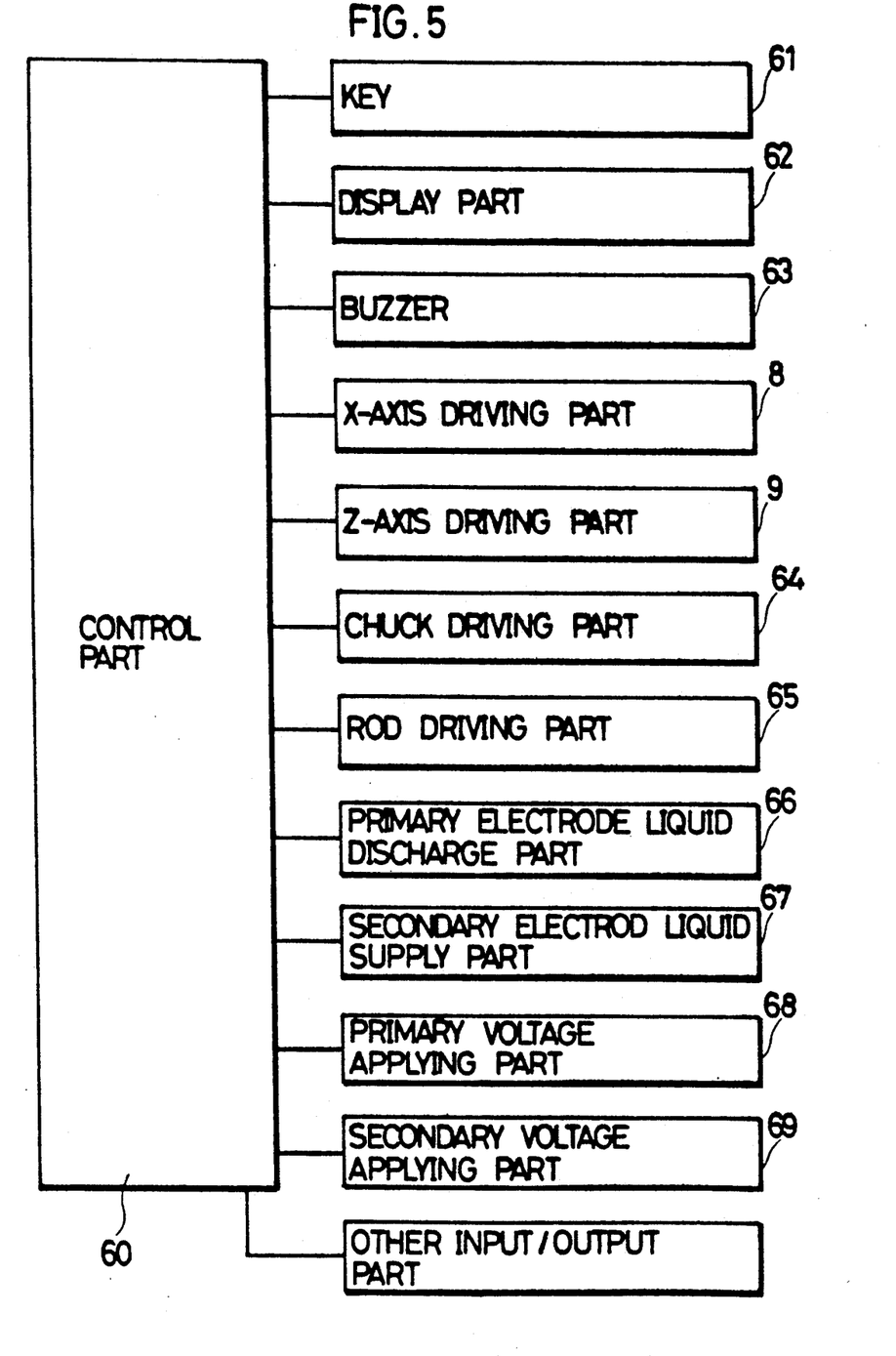
FIG. 5 is a schematic block diagram showing a control part of the electrophoresis apparatus.

FIG. 5 schematically shows a control part 60 of the two-dimensional electrophoresis apparatus 1. The control part 60 includes a microcomputer which is formed by a CPU, a ROM, a RAM and the like. The control part 60 is connected with various keys 61 which are arranged on the control panel 3 (FIG. 1), a display part 62 of an LCD, and a buzzer 63 for generating a warning sound. The control part 60 is also connected with the X-axis driving part 8 and the Z-axis driving part 9 shown in FIG. 2, a chuck driving part 64 including the motor 43 shown in FIG. 4, and a rod driving part 65 including the motor 48. The control part 60 is further connected with a primary electrode liquid discharge part 66 including a suction pump for discharging a primary electrode liquid through the discharge nozzle 50 (FIG. 4) etc., a secondary electrode liquid supply part 67 including a supply pump for supplying a secondary electrode liquid from the supply nozzle 37 to the upper reservoir 31 etc., a primary voltage applying part 68 for applying a voltage across the electrodes 25 and 26 of the first-dimensional electrophoresis part 5, and a secondary voltage applying part 69 for applying a voltage across the electrodes 35 and 36 of the second-dimensional electrophoresis part 6. The control part 60 is further connected with other input/output parts such as control parts for the temperature control blocks 24 and 34.

The operation of the two-dimensional electrophoresis apparatus 1 is now described with reference to flow charts shown in FIGS. 6 and 7.

Figure 6:
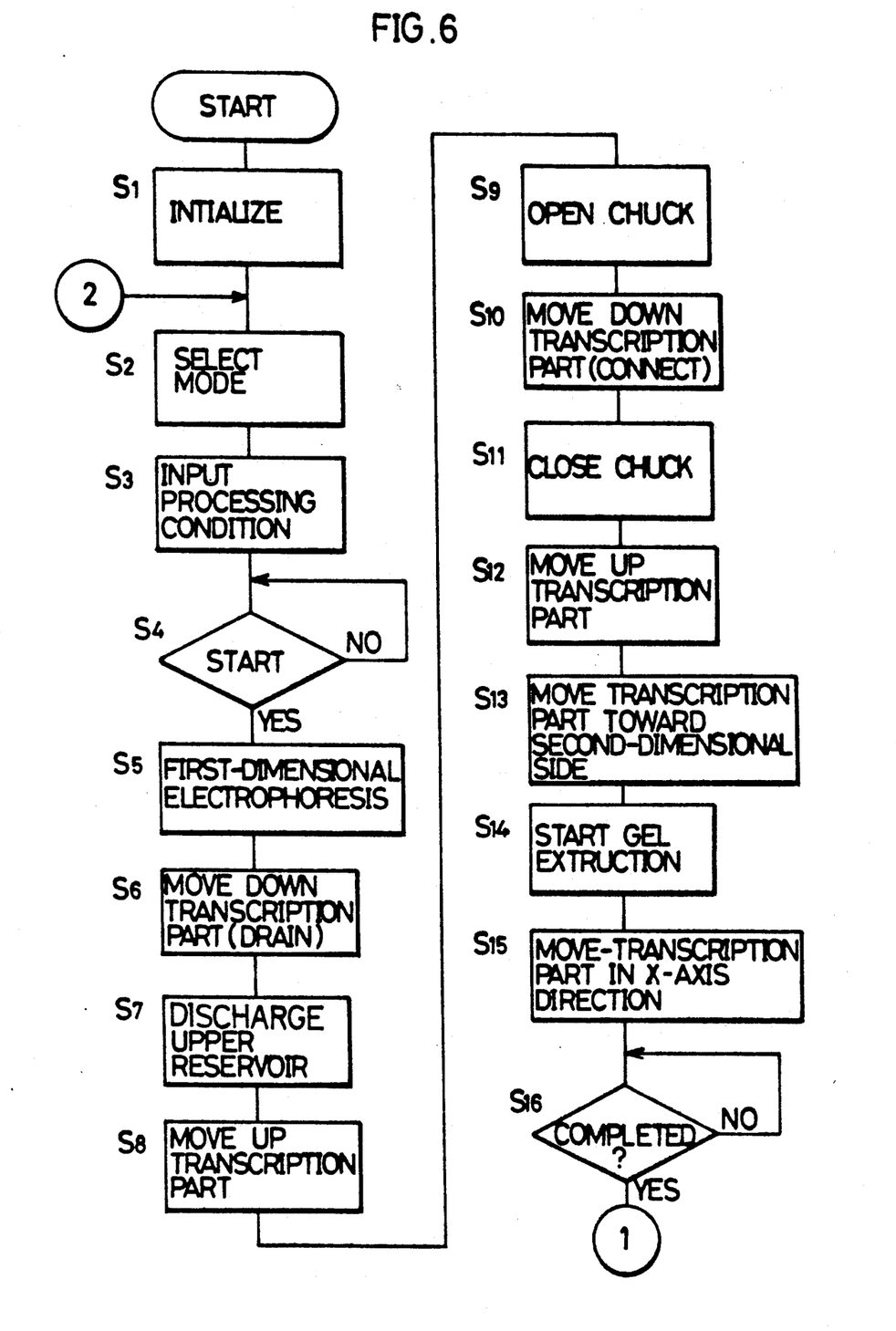
FIG. 6 is a control flow chart thereof.
Figure 7:
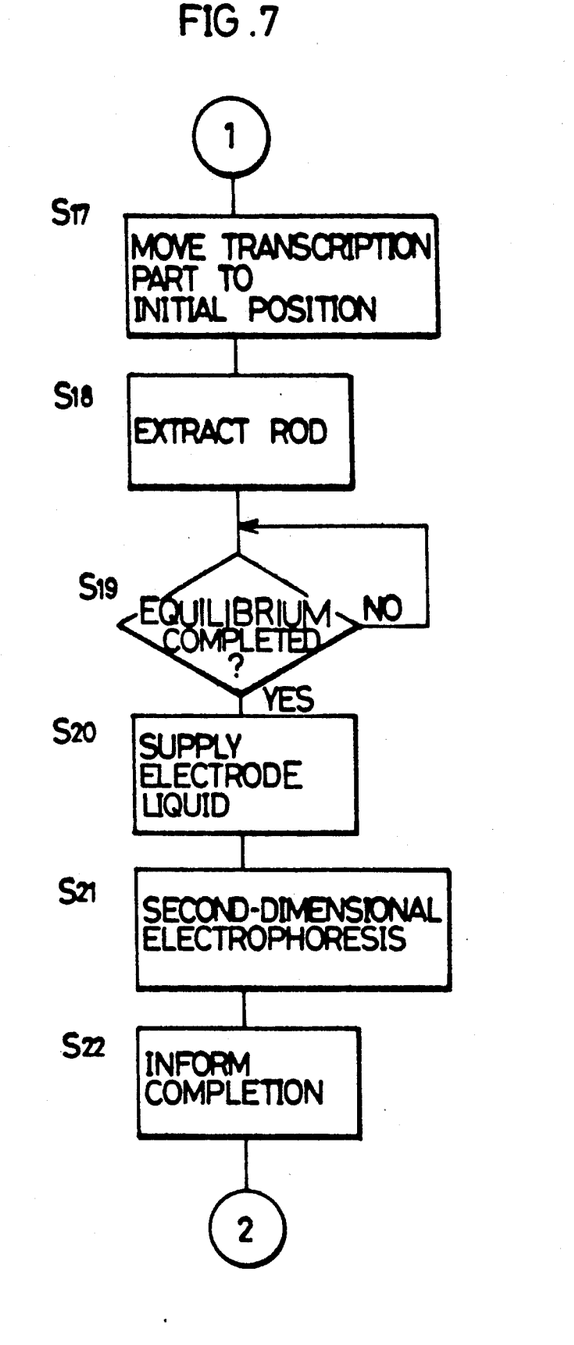
FIG. 7 is a control flow chart thereof.

When the program is started, initialization is made at a step S1 of FIG. 6 to arrange the transcription part 7 above the first-dimensional electrophoresis part 5 etc., and the process is advanced to a step S2. At the step S2, the operator operates the keys 61 of the control panel 3, to select an operation mode. For example, a desired electrophoresis mode is selected from modes of managing the electrophoresis state with time, with the product of voltage and time, with the product of current and time, and with the product of power and time, and the process is advanced to a step S3.

At the step S3, various processing conditions such as the processing time for the electrophoresis, the applied voltage and the like are inputted through the control panel 3. Then the process is advanced to a step S4, to wait for the operator pressing a start key.

The operor opens the front door 4, to set the housing 20, storing a gel which contains a sample, in the first-dimensional electrophoresis part 5, and introduces electrode liquids into the reservoirs 22 and 23. The operator further sets the housing 30 storing a slab gel in the second-dimensional electrophoresis part 6, introduces an electrode liquid only into the lower reservoir 32, and stores a equilibrium liquid in the upper end portion of the housing 30. When prescribed adjustment which is required for starting the electrophoresis is completed, the operator inputs a start command through the control panel 3. Upon receiving the start command, the process is advanced from the step S4 to a step S5.

Figure 8:
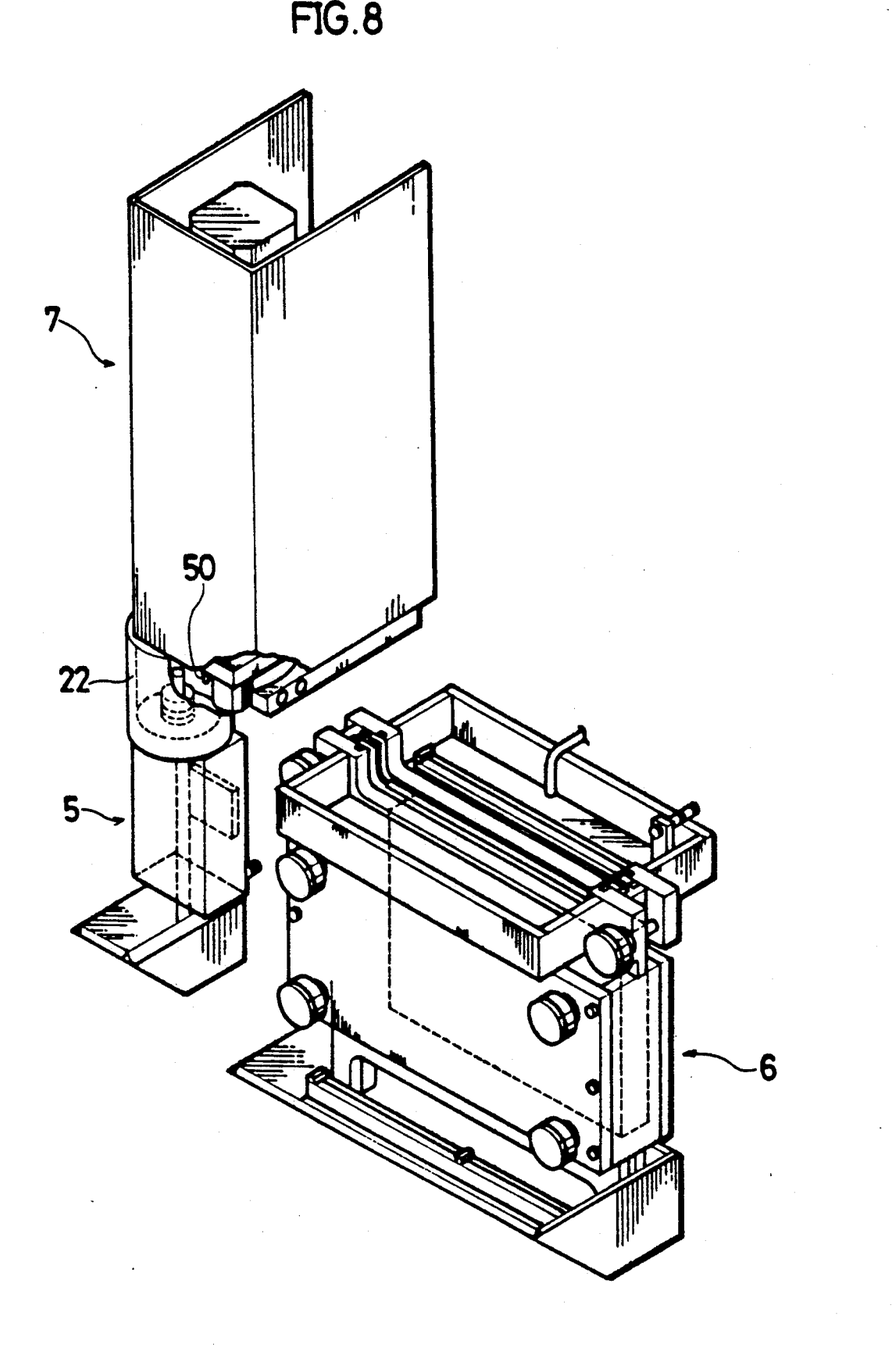
FIG. 8 is a perspective view corresponding to FIG. 3, showing a state of the apparatus in its operation.

At the step S5, a first-dimensional electrophoresis is executed on the basis of the processing mode and the processing conditions set at the steps S2 and S3. After the first-dimensional electrophoresis is completed, the process is advanced to a step S6. At the step S6, the transcription part 7 is downwardly moved to insert the discharge nozzle 50 into the upper reservoir 22 of the first-dimensional electrophoresis part 5, as shown in FIG. 8. At a step S7, the electrode liquid is discharged from the upper reservoir 22 through the discharge nozzle 50. Then the process is advanced to a step S8, to temporarily move up the transcription part 7.

At a step S9, the chuck 41 is opened. At a step S10, the transcription part 7 is downwardly moved toward the first-dimensional electrophoresis part 5. At this time, the transcription part 7 is so downwardly moved that the centering cylindrical member 49 engages with the upper end portion of the housing 20 in the upper reservoir 22. When the cylindrical member 49 engages with the upper end portion of the housing 20, the gel extrusion rod 44 is rendered concentric with the housing 20.

Figure 9:
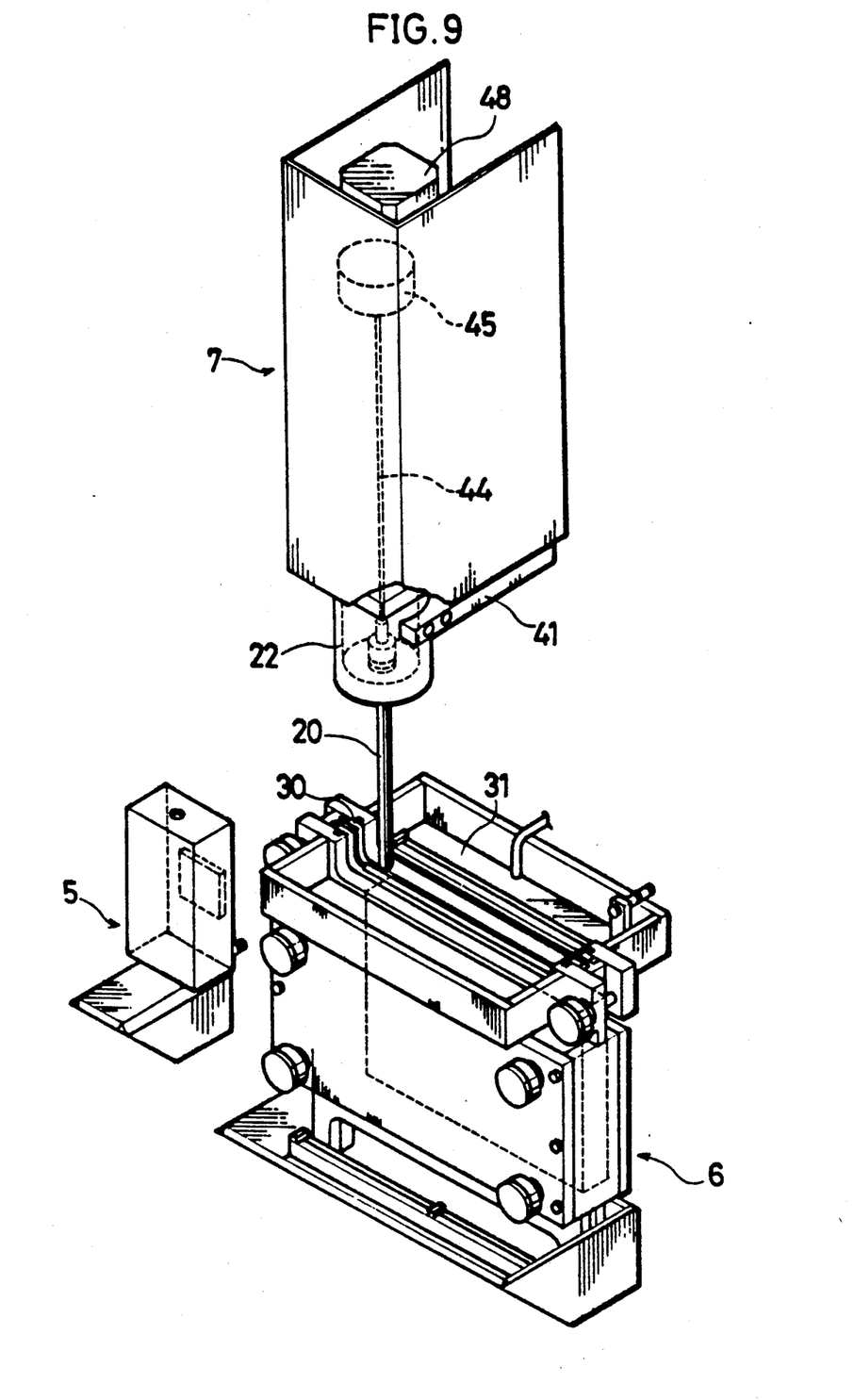
FIG. 9 is a perspective view corresponding to FIG. 3, showing another state of the apparatus in its operation.

At a step S11, the chuck 41 is closed to grasp the upper reservoir 22. At a step S12, the transcription part 7 is upwardly moved to move up the upper reservoir 22 with the chuck 41, so that the housing 20 is upwardly extracted from the temperature control block 24. When the housing 20 is completely extracted, the transcription part 7 is moved to a position above the second-dimensional electrophoresis part 6 at a step S13, as shown in FIG. 9.

Then the process is advanced to a step S14, to start downward movement of the gel extrusion rod 44. Thus, the rod 44 is inserted in the housing 20, to start downward extrusion of the gel from the housing 20. At a step S15, the transcription part 7 is moved in the X-axis direction along the housing 30. The distance of movement of the transcription part 7 along the X-axis direction coincides with the length of the gel extruded by the gel extrusion rod 44. Consequently, the gel completing the first-dimensional electrophoresis is arranged on the upper end portion of the housing 30.

Figure 10:
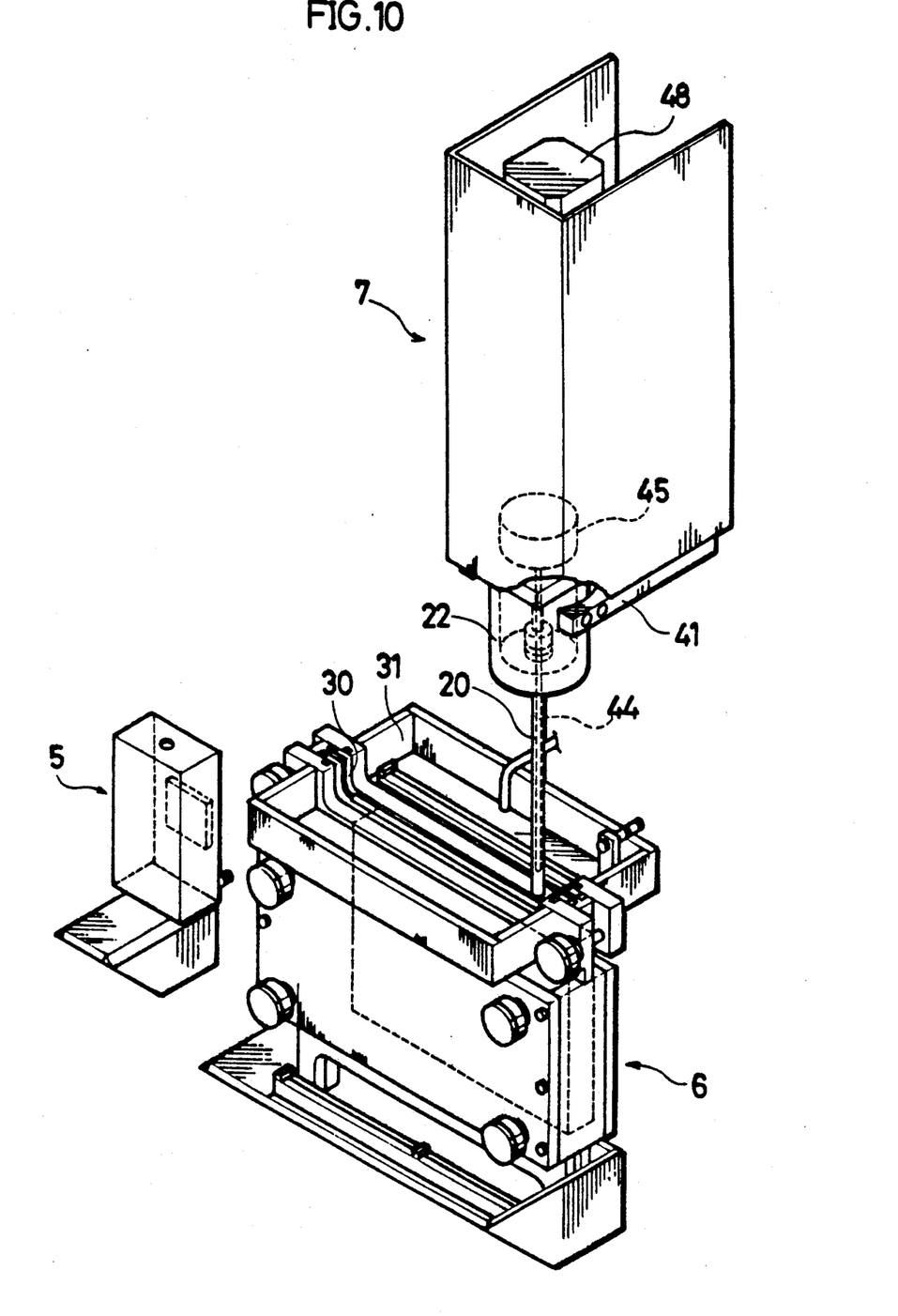
FIG. 10 is a perspective view corresponding to FIG. 3, showing still another state of the apparatus in its operation.

A step S16 is adapted to wait for completion of the gel extrusion started at the step S14 and the movement of the transcription part 7 in the X-axis direction started at the step S15. If a determination of yes is made at the step S16, the process is advanced to a step S17 shown in FIG. 7. At this time, the gel extruded from the housing 20 is dipped in the equilibrium liquid which is stored in the upper end portion of the housing 30. FIG. 10 shows an operation state attained when a determination of yes is made at the step S16.

At the step S17, the transcription part 7 is moved back to its initial position. At a step S18, the gel extrusion rod 44 is upwardly moved and extracted from the housing 20.

A step S19 is adapted to wait for completion of gel equilibrium with the equilibrium liquid on the housing 30 of the second-dimensional electrophoresis part 6. When a determination is made on completion of such equilibrium, the process is advanced to a step S20. At the step S20, the supply nozzle 37 supplies an electrode liquid into the upper reservoir 31. At a step S21, a prescribed voltage is applied across the electrodes 35 and 36, thereby executing a second-dimensional electrophoresis.

When the second-dimensional electrophoresis is completed, the process is advanced to a step S22 to sound the buzzer 63 and display completion of the processing on the display part 62. Then the process is returned to the step S2 shown in FIG. 6.

According to this embodiment, as hereinabove described, the transcription part 7 transfers the first-dimensional gel from the first-dimensional electrophoresis part 5 to the second-dimensional electrophoresis part 6 so that the second-dimensional electrophoresis is automatically executed, whereby it is possible to save labor as well as to improve reproducibility of separated images and separative power with no regard to skillfulness of the operator.

When no equilibrium is carried out, the operator may previously introduce an electrode liquid into the upper reservoir 31 of the second-dimensional electrophoresis part 6 in setting. In this case, it is possible to omit the supply nozzle 37 and the structure related thereto.

The temperature control blocks 24 and 34 comprising Peltier elements may be omitted and the lower reservoirs 23 and 32 may be increased in size to dip the housings 20 and 30 in the electrode liquids which are contained in the reservoirs 23 and 32, thereby controlling temperatures thereof. In this case, a temperature control part is used for adjusting the temperatures by circulating the electrode liquids contained in the lower reservoirs 23 and 32.

The two-dimensional electrophoresis apparatus according to the present invention comprises the gel transfer means for transferring the first-dimensional gel completely electrophoresed by the first-dimensional electrophoresis means from the first-dimensional gel housing to an end of the second-dimensional gel housing. According to the present invention, therefore, it is possible to automatically transfer the first-dimensional gel, thereby improving reproducibility of separated images and separative power with no regard to skillfulness of an operator.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A two-dimensional gel electrophoresis apparatus, comprising:

a first-dimensional gel housing storing a first-dimensional gel;

first-dimensional electrophoresis means for conducting a first-dimensional electrophoresis with said first-dimensional gel;

a second-dimensional gel housing storing a second-dimensional gel;

second-dimensional electrophoresis means for conducting a second-dimensional electrophoresis with said second-dimensional gel; and gel transfer means for transferring said first-dimensional gel after being electrophoresed by said first-dimensional electrophoresis means from said first-dimensional gel housing to one end of said second-dimensional gel housing, said gel transfer means comprising:

a grasping mechanism for grasping said first-dimensional gel housing, a moving mechanism for raising up a lower end of said first-dimensional gel housing to a position higher than an upper end of said second-dimensional gel housing and horizontally moving said first-dimensional gel housing longitudinally along the upper end of said second-dimensional gel, and an extrusion mechanism for extruding said first-dimensional gel from said first-dimensional gel housing following said horizontal movement of said first-dimensional gel housing by said moving mechanism at the same speed as said horizontal movement.

2. A two-dimensional electrophoresis apparatus in accordance with claim 1, wherein the upper end portion of said first-dimensional gel housing is fixed to an upper reservoir containing an electrode liquid, and said grasping mechanism of said gel transfer means grasps said first-dimensional gel housing through said upper reservoir.

3. A two-dimensional electrophoresis apparatus in accordance with claim 2, wherein said gel transfer means comprises drain means for discharging said electrode liquid from said upper reservoir of said first-dimensional gel housing.

4. A two-dimensional electrophoresis apparatus in accordance with claim 1, wherein
said extrusion mechanism comprises:
a vertically movable gel extrusion rod,
a vertical mechanism for vertically moving said rod, and
a centering member slidably supporting said rod for aligning center lines of said rod and said first-dimensional gel housing when said grasping mechanism grasps said first-dimensional gel housing.

5. A two-dimensional electrophoresis apparatus in accordance with claim 4, wherein
said vertical mechanism comprises:
a tapped holder fixed to the upper end of said rod and supported to be movable along a vertical guide shaft, and
a feed screw extending vertically, being adapted for screwing into said tapped holder, and being driven by a motor for vertically moving said holder.

6. A two-dimensional electrophoresis apparatus in accordance with claim 4, wherein
said first-dimensional gel housing is a cylindrical glass tube, and
said centering member is a cylindrical member whose inner diameter is equal to the outer diameter of said glass tube, so that said rod slides along its center.

7. A two-dimensional gel electrophoresis apparatus, said apparatus comprising:
a first-dimensional gel housing storing a first-dimensional gel;
first-dimensional electrophoresis means for conducting a first-dimensional electrophoresis with said first-dimensional gel;
a second-dimensional gel housing storing a second-dimensional gel;
second-dimensional electrophoresis means for conducting a second-dimensional electrophoresis with said second-dimensional gel; and
gel transfer means for transferring said first-dimensional gel after being electrophoresed by said first-dimensional electrophoresis means from said first-dimensional gel housing to one end of said second-dimensional gel housing, said gel transfer means including means for positioning and moving said first-dimensional gel housing adjacent one end of said second-dimensional gel housing and means for extruding said first-dimensional gel along one end of said second-dimensional gel while moving said first-dimensional housing.

8. An apparatus according to claim 7, wherein said positioning and moving means for said first-dimensional gel housing moves said first-dimensional housing along the one end of said second-dimensional housing at the same speed that the first-dimensional gel is extruded from said first-dimensional housing along the one end of said second dimensional-gel.

9. An apparatus according to claim 8, wherein said positioning and moving means positions a lower end of said first-dimensional gel housing above an upper end of said second-dimensional gel housing, and horizontally moves said first-dimensional gel housing longitudinally along an upper end of said second-dimensional gel while said extruding means extrudes said first-dimensional gel from said first-dimensional gel housing onto said second-dimensional gel.

10. A two-dimensional gel electrophoresis apparatus, said apparatus comprising:
a first-dimensional gel housing;
a first-dimensional gel disposed within said first-dimensional gel housing;
a second-dimensional gel housing;
a second-dimensional gel disposed within said second-dimensional gel housing;
an extruding device for extruding said first-dimensional gel from said first-dimensional gel housing directly along one end of said second-dimensional gel after said first gel has been electrophoresed.

11. An apparatus according to claim 10, wherein said extruding device includes a mechanism for moving said first-dimensional gel housing relative to said second-dimensional housing while extruding the first-dimensional gel along the one end of said second-dimensional gel.

12. An apparatus according to claim 11, wherein said mechanism moves said first-dimensional gel housing at the same speed as said first-dimensional gel is extruded from said first-dimensional housing to prevent changing a dimensional length of said first-dimensional gel while being extruded.

13. An apparatus according to claim 12, wherein said mechanism moves a lower portion of said first-dimensional gel housing above an upper portion of said second-dimensional gel housing in a horizontal direction while extruding said first-dimensional gel from said first-dimensional gel housing onto said second-dimensional gel.

* * * * *